United States Patent [19]

Laidler et al.

[11] 4,343,935
[45] Aug. 10, 1982

[54] CHIRAL COMPOUNDS

[75] Inventors: Dale A. Laidler, Huntington; David J. Milner, Manchester, both of England

[73] Assignee: Imperial Chemical Industries Limited, London, England

[21] Appl. No.: 166,837

[22] Filed: Jul. 8, 1980

[30] Foreign Application Priority Data

Jul. 13, 1979 [GB] United Kingdom ............... 7924520

[51] Int. Cl.$^3$ ............................................. C07D 213/53
[52] U.S. Cl. ................................. 542/414; 542/420; 542/422; 542/424; 546/2; 546/176; 546/268; 546/283; 546/329
[58] Field of Search ............... 546/329, 176, 283, 268, 546/2; 542/424, 422, 414, 420

[56] References Cited

U.S. PATENT DOCUMENTS

| | | | |
|---|---|---|---|
| 3,868,401 | 2/1975 | Aratani et al. | 260/468 H |
| 4,029,683 | 6/1977 | Aratani et al. | 260/438.1 |
| 4,029,690 | 6/1977 | Aratani et al. | 260/468 H |
| 4,119,652 | 10/1978 | Knowles | 546/2 |
| 4,124,533 | 11/1978 | Knowles | 546/2 |

FOREIGN PATENT DOCUMENTS 50-160241 12/1975 Japan .
1459285 12/1976 United Kingdom .

OTHER PUBLICATIONS

Adam et al. J. Chem. Soc. 1979, pp. 234–235.
Harai et al. Agric. Biol. Chem. 40(1976), pp. 169–174.
Aratani et al. Tet. Letters 1975, pp. 1707–1710, 1977 pp. 2599–2602.
Orioli et al. J. Am. Chem. Soc. 88 (1966), pp. 277–280.
MacDonald et al. Inorg. Chem. Acta 33(1979), p. L183.
Nakamura et al. J. Am. Chem. Soc. 100(1978), pp. 3443–3448, pp. 6544–6546.
Saconi et al. J. Chem. Soc. 1964, pp. 276–280.
Nozaki et al. Tetrahedron 24(1968), pp. 3655–3669.
Zassinovich J. Orgmet Chem. 133(1977), pp. 377–384.
Robinson et al. Inorg. Chem. 2(1963), pp. 1178–1181.
Hubert, Synthesis 9(1976), pp. 600–602.

Primary Examiner—Arthur P. Demers
Attorney, Agent, or Firm—Cushman, Darby & Cushman

[57] ABSTRACT

Chiral Schiff bases, and transition metal complexes thereof, of formula:

$$JN=CR^6-(CR^4R^5)_n \quad \text{[pyridine ring with } R^1, R^2, R^3\text{]} \quad (CR^4R^5)_n-CR^6=NK$$

wherein $R^1$, $R^2$ and $R^3$, which may be the same or different, are hydrogen, alkyl, aralkyl, aryl, alkaryl, a substituent containing a hetero atom, or two of $R^1$, $R^2$ and $R^3$ together with the pyridine ring from fused system, $R^4$ and $R^5$ which may be the same or different, are hydrogen, lower alkyl, or, where n is 1, may with the pyridine ring to which $CR^4R^5$ is attached form a fused system, $R^6$ is hydrogen, alkyl, aralkyl, aryl or alkaryl, n is 0, 1 or 2 and J and K, which may be the same or different, are groups of the formulae:

$$\begin{array}{cc} R^7 & R^8 \\ | & | \\ C^*-C-OH \\ | & | \\ H & R^8 \end{array}$$

in which C* is an asymmetric carbon atom, and $R^7$ and $R^8$, which may be the same or different, are alkyl, aralkyl, aryl or alkaryl, or $$\text{(CHOR}^{10})_m \text{—O—} \begin{array}{c} R^{11} \\ R^{12} \\ R^{13} \end{array} \text{(CHOR}^{14})_p \text{, } OR^9$$

in which at least the ring carbon atom to which the iminyl nitrogen atom is attached is asymmetric, at least one of the carbon atoms adjacent the said ring carbon atom bears a hydroxyl group, $R^9$ and $R^{14}$, which may be the same or different, are hydrogen or lower alkyl, $R^{10}$ is hydrogen, or lower alkyl, or together with $R^{15}$ forms a divalent hydrocarbyl group, $R^{11}$ is hydrogen, a sugar residue, or —CH$_2$OR$^{15}$ in which $R^{15}$ is hydrogen, lower alkyl or together with $R^{10}$ forms a divalent hydrocarbon group, $R^{12}$ is hydrogen or —CH$_2$OR$^{15}$ in which $R^{15}$ is hydrogen, or a lower alkyl, $R^{13}$ is hydrogen, OR$^1$, or a sugar residue, provided that both $R^{12}$ and $R^{13}$ are not hydrogen, m is 0, 1 or 2, p is 0 or 1 provided that m plus p is 0, 1, 2 or 3. The transition metal is for example copper (II), chromium (II), manganese (II), iron (II), cobalt (II), nickel (II) or palladium (II). The aforesaid complexes may be used as catalysts in the cyclopropanation of olefins by diazoacetates to form insecticide or insecticide precursors.

15 Claims, No Drawings

CHIRAL COMPOUNDS

This invention relates to novel chiral Schiff bases, to novel chiral metal complexes, and to the preparation of such bases and complexes, such complexes may be used as catalysts in the preparation of cyclopropane carboxylic acid esters which are compounds useful as insecticides, or insecticide intermediates.

It will be appreciated by those skilled in the art that cyclopropane carboxylic acid esters may, where the cyclopropane ring is appropriately substituted, exist in various geometrical and stereoisomeric forms. In particular the carbon atom bearing the carboxylic acid group may have the S or R configuration.

Moreover, it is known that, where insecticides are derived from cyclopropane carboxylic acids, the isomer having the 1R configuration is insecticidally more effective than its stereoisomer having the 1S configuration.

Cyclopropane carboxylic acid esters which are insecticides or insecticide precursors may be prepared by the reaction of an ester of diazoacetic acid with a carbon-carbon double bond of a suitable monoene or a diene. It is known that where this reaction is catalysed by chiral copper complexes an enantiomeric excess of esters having a predetermined configuration may be obtained. United Kingdom Patent Specification No. 1455189 and Japanese Patent Kokai No. 160241/75 disclose the preparation of cyclopropane carboxylic acid esters useful as insecticide intermediates from dienes using copper complexes of Schiff bases as catalysts. The Schiff bases were derived from salicylaldehydes, or derivatives thereof, and notional derivatives of amino-acids.

We have now found that the reaction of diazoacetic ester with a suitable monoene or diene may be catalysed by certain novel chiral metal complexes and that an enantiomeric excess of cyclopropane carboxylic acid esters having a predetermined configuration may be obtained. Moreover, where a monoene is used an excess of the cis isomers is often formed. In the novel chiral metal complexes the metal is co-ordinated with a novel chiral Schiff base derived from a heterocyclic di-carbonyl compound and two chiral amines, which may be the same or different, which chiral amines have (a) an asymmetric carbon atom which bears the amino group and (b) a hydroxyl group on the carbon atom adjacent the aforesaid asymmetric carbon atom.

In one aspect therefore the present invention provides chiral Schiff bases according to the general formula:

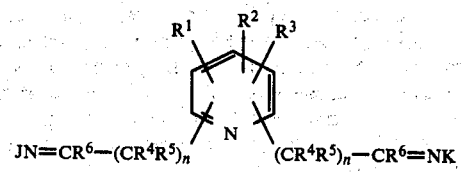

and transition metal (as hereinafter defined) complexes thereof
wherein
$R^1$, $R^2$ and $R^3$, which may be the same or different, are hydrogen, alkyl, aralkyl, aryl, alkaryl, a substituent containing a hetero atom, or two of $R^1$ $R^2$ and $R^3$ together with the pyridine ring form fused system,
$R^4$ and $R^5$, which may be the same or different, are hydrogen, lower alkyl, or, where n is 1, may with the pyridine ring to which $CR^4R^5$ is attached form a fused system,
$R^6$ is hydrogen, alkyl, aralkyl, aryl or alkaryl, n is 0, 1 or 2
and J and K, which may be the same or different, are groups of the formulae:

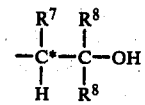

in which C* is an asymmetric carbon atom, and $R^7$ and $R^8$, which may be the same or different, are alkyl, aralkyl, aryl or alkaryl,

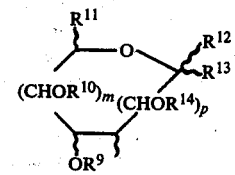

in which at least the ring carbon atom to which the iminyl nitrogen atom is attached is asymmetric, at least one of the carbon atoms adjacent the said ring carbon atom bears a hydroxyl group, $R^9$ and $R^{14}$, which may the same or different, are hydrogen or lower alkyl,
$R^{10}$ is hydrogen, or lower alkyl, or together with $R^{15}$ forms a divalent hydrocarbyl group
$R^{11}$ is hydrogen, a sugar residue, or —$CH_2OR^{15}$ in which $R^{15}$ is hydrogen, lower alkyl or together with $R^{10}$ forms a divalent hydrocarbon group,
$R^{12}$ is hydrogen or —$CH_2OR^{15}$ in which $R^{15}$ is hydrogen, or a lower alkyl,
$R^{13}$ is hydrogen, $OR^1$, or a sugar residue, provided that both $R^{12}$ and $R^{13}$ are not hydrogen,
m is 0, 1 or 2
p is 0 or 1 provided that m plus p is 0, 1, 2 or 3, and the corresponding compounds having an oxygen atom attached to the pyridine ring nitrogen.

By lower alkyl group we mean an alkyl group having up to five carbon atoms, e.g. methyl, ethyl, n-propyl and n-butyl.

Examples of alkyl groups represented by $R^1$, $R^2$, $R^3$ and $R^6$ are methyl, ethyl, n-propyl, iso-propyl, n-butyl, isobutyl, sec-butyl, tert-butyl, n-pentyl, n-hexyl, cyclohexyl, n-octyl, 2-ethylhexyl, n-decyl and n-dodecyl.

Where $R^1$, $R^2$ or $R^3$ contain one or more heteroatoms, specific examples include OH, $OR^{16}$, $OCOR^{16}$, CHO, $COR^{16}$, $CO_2R^{16}$, CN, $CONH_2$, $NH_2$, $NHR^{16}$, $NR_2^{16}$, $NHCOR^{16}$, $NO_2$, SH, $SR^{16}$, $SOR^{16}$, $SO_3H$, $SO_3R^{16}$ or a halogen atom, wherein $R^{16}$ is alkyl, aralkyl or aryl.

Examples of aralkyl groups represented by $R^6$ are benzyl and 2-phenylethyl.

Preferably $R^1$, $R^2$, $R^3$ and $R^6$ are hydrogen and n is 0.

Examples of substituents $R^7$ and $R^8$ in general formula II are methyl, ethyl, propyl, isopropyl, butyl, isobutyl, 2-butyl, tert-butyl, octyl, cyclohexyl, cyclohexylmethyl, benzyl, benzhydryl, 2,2-diphenyl-ethyl, phenyl, tolyl and naphthyl.

In compounds of formula I in which groups J and K are represented by formula II, preferably $R^7$ is a phenyl group and $R^8$ is a substituted phenyl group. It is also preferred that $R^8$ represents a phenyl group having a substituent at the 2-position or having substituents at the 2,5- or 2,6- position. Examples of substituted phenyl groups are 2-methoxyphenyl, 2-ethoxyphenyl, 2-propoxyphenyl, 2-isopropoxyphenyl, 2-butoxyphenyl, 2-tert-butoxyphenyl, 2-octyloxyphenyl, 2-benyloxyphenyl, 2-phenoxyphenyl, 2-methoxy-5-methyl-phenyl, 2-butoxy-5-methylphenyl, 2-benzyloxy-5-methylphenyl, 5-tert-butyl-2-methoxyphenyl, 2-butoxy-5-tert-butylphenyl, 5-tert-butyl-2-octyloxyphenyl, 2-benzyloxy-5-tert-butylphenyl, 4-methoxy-biphenyl-3-yl, 2,5-dimethoxyphenyl, 2,5-dibutoxyphenyl, 2,5-dioctyloxyphenyl, and 2,5-dibenzyloxyphenyl.

It will be appreciated that where a monosaccharide is used as a substituent J and/or K the monosaccharide which, in general formula III, is shown in the cyclic hemiacetal or hemiketal form may exist in equilibrium with the corresponding open-chain form having a free carbonyl group. Moreover, while the monosaccharide may exist in the furanose form (five membered ring) the pyranose form is usually more stable for the free monosaccharide.

Where groups J and K are represented by Formula III and $R^{10}$ and $R^{15}$ together form a divalent hydrocaryl group the divalent hydrocarbyl group typically is part of a cyclic acetal, e.g. it is methylene, ethylidene, or benzylidene; or a cyclic ketal e.g. isopropylidene, or forms a polyalkylene bridge between oxygen atoms of the monosaccharide, e.g. it is ethylene or propylene.

Where groups J and K are represented by formula III preferably p is 0, m is 1, $R^9$ is hydrogen, $R^{10}$ is hydrogen or with $R^{15}$ forms a divalent hydrogen group, $R^{11}$ is —$CH_2OR^{15}$, $R^{12}$ is hydrogen, $R^{13}$ is lower alkoxy, e.g. methoxy, particularly preferably they have the general structure represented by the modified Haworth projection formula:

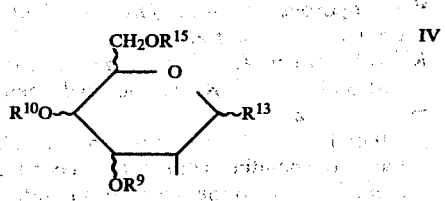

IV i.e. the configuration of the ring carbon atom to which the iminyl nitrogen atom is attached (C2 of the pyranose ring in formula IV) is R, where $R^{13}$ is lower alkoxy and $R^{10}$ and $R^{15}$ are both hydrogen, alkyl groups or together form a divalent hydrocarbon group; since we have found that chiral Schiff bases according to the invention in which the pyranose ring has the configuration at C2 (the carbon bearing the nitorgen atom of the iminyl group) specified in general formula IV form metal complexes which, when employed as catalysts in the process according to the present invention often give preferentially cyclopropane carboxylic acid esters having the 1R configuration.

Examples of specific amino-monosaccharides from which, or from derivatives of which, novel chiral Schiff bases according to the present invention may be prepared, include inter alia 2-amino-2-deoxy-D-glucose, 2-amino-2-deoxy-D-allose, 2-amino-2-deoxy-D-galactose, 2-amino-2-deoxy-D-altrose, 2-amino-2-deoxy-D-mannose, 2-amino-2-deoxy-D-ribose and 2-amino-2-deoxy-D-xylose.

Examples of specific heterocyclic carbonyl compounds from which novel chiral Schiff bases according to the present invention may be prepared include inter alia 2,6-pyridinedicarboxaldehyde and 2,6-diacetylpyridine.

Where it is desired to form a novel chiral Schiff base of the present invention from an enantiomer of a chiral amine having a hydroxyl group on the carbon atom adjacent the carbon atom bearing the amino group the aforesaid enantiomer may be obtained by, for example, optical resolution of a mixture of the appropriate enantiomers. Preferably, however, the aforesaid enantiomer is prepared from an entantiomer of a chiral starting material. Naturally occuring α-amino acid esters are one class of convenient starting materials and they may be converted into suitable chiral amines by the known reaction with appropriate Grignard reagents. An example of a preferred amino alcohol derived from an amini acid is 2-amino-1,1-di-(2-methoxyphenyl)-3-phenylpropan-1-ol. Naturally occurring monosaccharides provide a second class of convenient starting materials.

The compounds of formula I having an oxygen atom on the ring nitrogen may be obtained by oxidation of the corresponding compounds of formula I in which the ring nitrogen is unsubstituted. A suitable oxidising agent for this purpose is hydrogen peroxide.

It is believed that the chiral transition metal complexes according to the present invention have structures represented by the general formula:

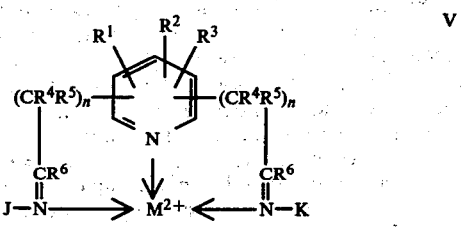

V wherein $R^1$, $R^2$, $R^3$, $R^4$, $R^5$, $R^6$, J, K and n have the meanings previously ascribed to them, and M is a metal from the first or second series of the main group of transition metals.

By transition metal we mean a metal which, in any one of its commonly occurring oxidation states, has a partly filled d shell only. In the first series the partly filled d shell is 3 d and in the second series the partly filled d shell is 4d.

Preferably the metal is copper (II), chromium (II) manganese (II), iron (II), cobalt (II), nickel (II) or palladium (II). Particularly preferably the metal is copper (II).

It will be appreciated that in chiral metal complexes according to the present invention the metal carries a positive charge and an anion is necessary to provide an electrically neutral compound. The anions associated with the metal complexes may be inorganic or organic, provided that they are derived from strong acids having a $pK_a$ value less than 2.5.

The anions should not be oxidising or reducing agents or otherwise chemically reactive with diazo compounds or other materials used in the preparation of the cyclopropane derivatives. Suitable anions include inter alia halide, fluoroborate, methyl sulphate, bisulphate, aromatic sulphonates, fluorosilicate, sulphate, tetrafluoroborate and tetraphenylborate.

Amino-sugars useful for the preparation of chiral Schiff bases according to the invention may be naturally occurring, e.g. D-glucosamine, or D-mannosamine, or they may be prepared from monosaccharides or from naturally occurring amino-monosaccharides. One known synthetic route to aminosugars is via anhydro-monosaccharides as indicated by the following reaction sequence:

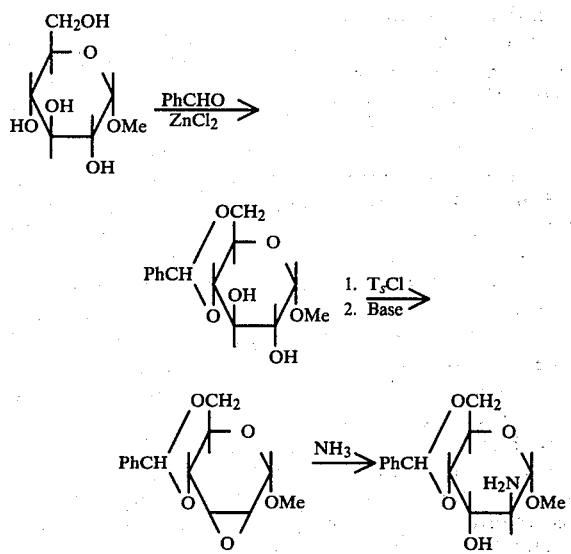

which illustrates the conversion of methyl α-D-glucoside into a derivative of 2-deoxy-2-amino-D-altrose. As examples of other conversions which may be effected by the above reaction sequence we may mention the conversion of D-idose into a derivative of 2-deoxy-2-amino-D-galactose and the conversion of D-arabinose into a derivative of 2-deoxy-2-amino-D-xylose.

Another synthetic route involves the sequence:

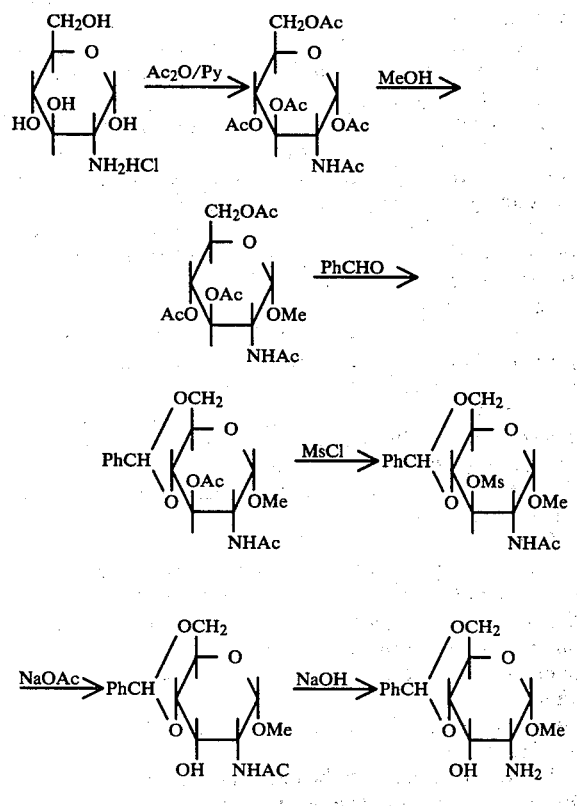

which illustrates the conversion of 2-deoxy-2-amino-D-glucose into a derivative of 2-deoxy-2-amin-D-allose.

The novel chiral Schiff bases according to the present invention are conveniently prepared by reacting a chiral primary amine with a heterocyclic di-carbonyl compound. Preferably the carbon atom adjacent the carbon atom bearing the amino group bears a hydroxyl group or a protected hydroxyl group, more preferably a hydroxyl group. The reaction is preferably carried out in the presence of an inert solvent in which the Schiff base is insoluble and is effected near the reflux temperature of the solvent.

Suitable solvents include aromatic hydrocarbons e.g. toluene, alcohols, e.g. methanol and chlorinated hydrocarbons.

Various methods are available for preparing novel transition metal complexes of chiral Schiff bases according to the present invention. For example, a novel chiral Schiff base may be treated with a transition metal inorganic salt, e.g. copper (II) chloride, to form the corresponding complex, and then, where it is desired to form a fluoroborate, with a suitable fluoroborate, typically in excess e.g. sodium fluoroborate, to form the corresponding fluoroborate complex (hereinafter Method A). A solution of a chiral Schiff base according to the present invention, preferably in a suitable solvent, e.g. warm methanol, may be added to a suspension of a suitable transition metal complex, e.g. bis(salicylaldehydato) copper (II), in a suitable solvent, e.g. methanol, and the resulting mixture stirred to form a novel chiral complex according to the present invention (hereinafter Method B). A chiral Schiff base according to the present invention and a transition metal carboxylate, e.g. copper (II) acetate, preferably dissolved in a suitable solvent, e.g. ethanol, may be heated, preferably under reflux where a suitable solvent is used, for an appropriate time, e.g. 10 minutes; removal of the solvent, where it is used, leaves a binuclear transition metal complex according to the present invention (hereinafter Method c).

Accordingly a further aspect of the present invention provides a method for the preparation of novel chiral metal complexes which method comprises (a) reacting a novel chiral Schiff base according to a first aspect of the present invention with a transition metal inorganic salt to form the corresponding transition metal complex and then optionally with a suitable fluoroborate to form the corresponding transition metal fluoroborate complex, or (b) reacting a novel chiral Schiff base according to a first aspect of the present invention with a suitable transition metal complex, or (c) reacting a novel chiral Schiff base according to a first aspect of the present invention with a transition metal carboxylate.

The chiral metal complexes according to the present invention may be employed as catalysts in the preparation of cyclopropanecarboxylic acid esters of general formula:

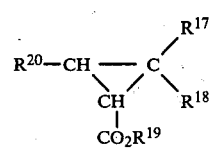

by reacting a compound having the general formula:

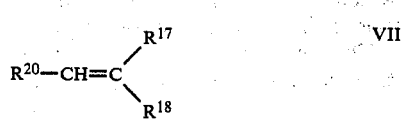

with an ester of diazoacetic acid.

In the formula VI and VII above:

$R^{17}$ represents a hydrogen atom or a lower alkyl group, $R^{18}$ represents a lower alkyl group, $R^{19}$ represents a lower alkyl group, or a group which forms insecticidally active esters with chrysanthermic acid e.g. 3-phenoxybenzyl or α-substituted 3-phenoxybenzyl and $R^{20}$ represents:

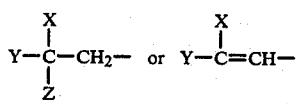

in which Z represents fluorine, chlorine or bromine X and Y, which may be the same or different represent fluorine, chlorine or bromine, lower alkyl group, $Q(CF_2)q$- (in which Q is hydrogen, fluorine or chlorine and q is 1 or 2) or

where each of U, V, W independently represents an atom of hydrogen, fluorine or chlorine except that where one of X and Y represents a group or formula $Q(CF_2)_2$—where Q is defined above, the other of X and Y represents an atom of fluorine, chlorine or bromine or a group of formula:

where U, V and W are as defined above.

Although the chiral metal complexes according to the present invention may be used for the preparation of many of the compounds of formula VI they are particularly useful for the preparation of compound wherein $R^{17}$ and $R^{18}$ are methyl, $R^{19}$ is ethyl, 3-phenoxybenzyl, α-cyano-3-phenoxybenzyl or α-ethymyl-3-phenoxybenzyl, and $R^{20}$ is $Cl_2C=CH-$, $CF_3CCl=CH-$, $CF_3CCl_2CH_2-$, $Cl_3C-CH_2-$, or $(CH_3)_2C=CH-$.

The use of the novel chiral complexes of the present invention as catalysts in the reaction of suitable monoenes or dienes with a diazoacetate ester to form insecticides or insecticide intermediates is more fully described in our copending United Kingdom Patent Application Nos. 7924521 and 7924522 respectively.

Compounds of general formula VI wherein $R^{17}$ and $R^{18}$ represent methyl, $R^{19}$ represents 3-phenoxybenzyl or α-cyano-3-phenoxybenzyl and $R^{20}$ represents $CCl_2=CH-$ are known to be potent insecticides when they have the 1R configuration; the isomers having the so-called 1R cis configuration being particularly potent and having more insecticidal activity than the isomers having the 1R trans configuration. The isomers having the 1S configuration have less insecticidal activity. By cis we mean that the hydrogens at C1 and C3 of the cyclopropane ring are in the cis relationship to one another and by trans we mean that the hydrogens at C1 and C3 of the cyclopropane ring are in the trans relationship to one another.

The reaction of a compound of general formula VII with a diazoacetate is preferably carried out in the presence of an inert solvent in which the cyclopropane product of formula VI is soluble.

Conveniently the solvent used is immiscible with water to facilitate preparation of the diazoacetic ester. More preferably the solvent also has a boiling point lower than that of the monoene or diene of formula VII to facilitate recovery of unreacted monoene or diene.

Suitable solvents include saturated chlorinated hydrocarbon solvents, such as ethylene dichloride, dichloromethane, tetrachloroethane, carbon tetrachloride and the like and hydrocarbon solvents such as toluene.

A wide variety of metal complexes according to the present invention may be used as catalyst, the precise 1R:1S ratio of the product being dependent inter alia upon the actual complex used.

The concentration of catalyst in the reaction mixture is not critical, but generally concentrations in the range 0.00001 to 1 g atoms of transition metal per liter of reaction mixture, and especially 0.005 to 1 g atoms, are suitable.

The temperature of reaction is generally in the range 0° C. to 130° C., preferably 10° C. to 90° C.

The diazoacetic acid ester may be prepared by reacting a water soluble acid addition salt (e.g. the hydrochloride of an ester of glycine) with an alkali metal nitrite in an aqueous medium which is stirred with a water-immiscible solvent into which the diazoacetic acid ester is extracted. Alkali metal nitrites which may be used, are for example, the potassium or sodium salts, and the reaction with the glycine ester is preferably carried out in the presence of an acid catalyst, for example, sulphuric acid.

The solution of diazoacetic acid ester thus formed is then added to a solution of the monoene or diene of formula VII maintained at the desired temperature, and containing the catalyst, usually in solution.

The ratio of monoene or diene to diazoacetic ester employed in processes hereindisclosed is normally in the range 1:10 to 10:1. It is usual to use enough monoene or diene to react with all the diazoacetate. However, where high conversions of monoene or diene to cyclopropane derivative are desired an excess of diazoacetate may be employed.

Progress of the reaction may be monitored by measuring nitrogen evolution, which may also be used to determine yield of total products, the proportion of the desired product being readily determined by gas liquid chromatography (g.l.c.).

Separation of the desired product from the reaction mixture may be achieved by any convenient means but it is generally convenient to first distil off the solvent, the monoene or diene, then any esters of maleic and fumaric acids and finally the required product. Alternatively, the crude product, where it is a lower alkyl ester, after removal of solvent and unreacted monoene or diene may be used as an intermediate without further purification.

The reaction may also be performed continuously by forming the diazoacetic ester in a first vessel and continuously transferring it, in a solvent, to a second vessel where it is reacted immediately with the monoene or diene, as described and claimed in our British Pat. No. 1,459,285.

It may sometimes be difficult to predict which optical isomer of a particular amino-acid or which stereoisomer of a particular amino-sugar constitution (from which the chiral metal complexes according to the present invention are notionally derived) will give an enhanced proportion of the desired optical isomer of the cyclopropane product; but this may be readily determined experimentally by testing each optical isomer in turn and determining the product distribution, e.g. by g.l.c. analysis.

We have found that where chiral metal complexes according to the present invention which are notionally derived from S-amino acids, which are often the naturally occurring isomers; are used to catalyse the reaction of a diagoacetate with a monoene an excess of cis cyclopropane isomers over trans cyclopropane isomers is formed and, at least, in the cis pair of enantiomers an excess of the 1R enantiomer is formed.

Our process may be used to produce a variety of esters of a particular cyclopropane carboxylic acid, the particular ester produced being dependent upon the particular glycine ester used. Thus the process may be used to produce simple alkyl esters, which are useful as intermediates in the preparation of insecticides, or it may be used to produce the insecticides themselves. In the latter case the glycine ester must correspond to the required insecticidal ester. Examples of glycine esters of this type include the ester with 3-phenoxybenzyl alcohol, and with 5-benzyl-3-furyl methanol.

The invention will now be illustrated by the following examples.

EXAMPLE 1

This example illustrates the preparation of a novel chiral Schiff base.

A mixture of S-2-amino-1,1-di(2-methoxyphenyl)-3-phenyl-1-propanol (2.01 g:5.54 m mole) (prepared by the method of A. McKenzie, R. Roger and G. O. Wills, J. Chem. Soc., 1926, 779) and 2,6-pyridinedicarboxaldehyde (0.374g:2.77 m mole) (prepared by the method of E. Papadopoulos, A. Jarrow and C. H. Issidorides, J. Org. Chem., 1966, 31, 615) was heated at reflux in absolute alcohol (100 ml) for 3 hours. Thin layer chromatography on silica gel using ether as eluant indicated a single product and no starting materials. Decolourizing charcoal was added to the reaction mixture which was then heated for a further 1 hour. The reaction mixture was filtered and the filtrate was evaporated to approximately one-third of its volume. Addition of n-hexane to the concentrated filtrate gave a precipitate which was filtered off and dried (1.51 g; 65% yield) m.p. 160°-161° C. The $^1$Hnmr spectrum of the precipitate was consistent with the structure:

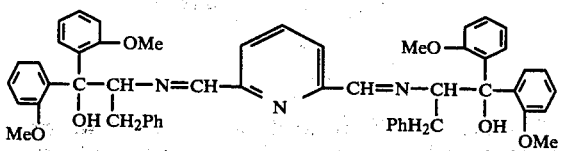

EXAMPLE 2

This example illustrates the preparation of a novel transition metal chiral complex.

To a solution of the chiral Schiff base (0.447 g 5.42 m mole) prepared as in Example 1, in warm ethanol (20 ml) was added dropwise with stirring over 15 minutes a solution of copper (II) chloride dihydrate (0.092 g:5.4 m mole) in water (5 ml). During the addition the colour of the reaction mixture changed from pale yellow to green. The reaction mixture was evaporated to dryness and the resulting green solid was recrystallised from dichloromethane-hexane to give pale green crystals (0.47 g:90% yield) mp.p. 166°-168° C. (dec.)

Elemental analysis for $C_{53}H_{51}N_3O_6 CuCl_2$:

|  | C | H | N | Cu |
|---|---|---|---|---|
| Found: | 64.21 | 4.54 | 3.62 | 7.2 |
| Calculated: | 66.28 | 5.35 | 4.38 | 6.6 |

EXAMPLE 3

This example illustrates the use of a novel complex according to the present invention as a catalyst in the reaction of a diazoacetic ester with a halogenated monoene of general formula VII.

2,2-dichloro-5-methyl-1,1,1-trifluorohex-4-ene (1.25 g) and a copper (II) complex of the Schiff base derived from 2,6-pyridinedicarboxaldehyde and S-2-amino-1,1-di(2-methoxyphenyl)-3-phenyl-1-propanol (0.04 mg atoms of copper) prepared as in Example 2 were stirred in toluene (10.0 ml) at 80° C. under an atmosphere of nitrogen. A burette was charged with a solution comprising the same olefine (1.25 g) ethyl diazoacetate (1.4 ml of a standard toluene solution; 1.94 m mole) and toluene (5.0 ml). This solution was added to the solution of catalyst in olefin at a constant rate of approximately 1.3 ml per hour, and the nitrogen evolved during the reaction was collected. After 20 hours at 80° C. the addition of the diazoacetate and olefine solution was complete and the volume of nitrogen collected was 45 ml (approximately 100% of theoretical nitrogen evolved for total decomposition of the ethyl diazoacetate). The isomer ratio determined by glc of the 2-d-octyl esters was:

| 1R cis | 38%, |
| 1S cis | 22%, |
| 1R trans | 20%, |
| 1S trans | 20%. |

From these results it can be seen that where the reaction of 2,2-dichloro-5-methyl-1,1,1-trifluorohex-4-ene with diazoacetic acid ethyl ester is catalysed by a chiral copper complex according to the present invention which is notionally derived from an S-amino acid an excess of cis cyclopropane isomers is formed and in the cis pair of enantiomer an excess of the 1R enantiomers is formed.

EXAMPLE 4

This example illustrates the use of the novel chiral metal complex prepared in Example 2 as a catalyst in the reaction of a diazoacetic acid ester with a halogenated diene of general formula VII.

1,1-Dichloro-4-methyl-1,3-pentadiene (3.0 g, 20 mM) and the catalyst described in Example 2 (0.096 g, 0.1 mM) were stirred together in toluene (10.0 ml) at 75° C. under an atmosphere of nitrogen. A solution comprising the diene (3.0 g, 20 mM), ethyl diazoacetate (5.8 ml of a standard toluene solution containing 8.0 mM of the azo compound) and toluene (10.0 ml) was added dropwise at the rate of 1.2 ml/h. After 20 hours the volume of nitrogen evolved (160 ml) was virtually quantitative for total consumption of the diazoacetate. Glc analysis of the 2-d-octyl esters gave the following data.

Yield of cyclopropane products (based on 100% consumption of diazoacetate) 37%
Cis: trans ratio 42:58
Isomer distribution:

| | |
|---|---|
| cis—1R | 24%: |
| cis—1S | 18%: |
| trans 1R | 30%: |
| trans 1S | 28%. |

From these results it can be seen that where the reaction of 1,1-dichloro-4-methyl-1,3-pentadiene with diazoacetic acid ethyl ester is catalysed by a chiral copper complex according to the present invention which is notionally derived from an S amino-acid an excess of the 1R enantiomer is formed in the cis pair of enantiomers and in the trans pair of enantiomers.

EXAMPLE 5

This example illustrates the use of the novel chiral metal complex prepared in Example 2 on a catalyst in the reaction of a diazoacetic ester with a halogenated monoene of general formula VII.

The procedure of Example 3 was repeated except that 1,1,1-trichloro-4-methyl-5-pentene was used instead of 2,5-dichloro-5-methyl-1,1,1-trifluorohex-4-ene. The isomer ratio obtained was:

| | |
|---|---|
| 1R cis | 30%: |
| 1S cis | 25%: |
| 1R trans | 24%: |
| 1S trans | 21%. |

From these results it can be seen that where the reaction of 1,1,1-trichloro-4-methyl-5-pentene with alkyl diazoacetate is catalysed by a chiral copper complex according to the present invention which is notionally derived from an S-amino-acid an excess of cis cyclopropane isomer is formed and in the cis pair of enantiomers and in the trans pair of enantiomers an excess of the 1R enantiomer is formed.

What we claim is:

1. A chiral Schiff base according to the general formula:

$$JN=CR^6-(CR^4R^5)_n \overset{R^1 \quad R^2 \quad R^3}{\underset{N}{\bigcirc}} (CR^4R^5)_n-CR^6=NK$$

wherein $R^1$, $R^2$ and $R^3$, which may be the same or different, are hydrogen, alkyl, aralkyl, aryl, alkaryl, hydroxyl, $OR^{16}$, $OCOR^{16}$, CHO, $COR^{16}$, $CO_2R^{16}$, CN, $CONH_2$, $NH_2$, $NHR^{16}$, $NR_2^{16}$, $NHCOR^{16}$, $NO_2$, SH, $SR^{16}$, $SOR^{16}$, $SO_3H$, $SO_3R^{16}$ wherein $R^{16}$ is alkyl, aralkyl or aryl, and halogen, $R^4$ and $R^5$, which may be the same or different, are hydrogen, lower alkyl, $R^6$ is hydrogen, alkyl, aralkyl, aryl or alkaryl, n is 0, 1 or 2 and J and K, which may be the same or different, are groups of the formulae:

$$-\overset{R^7}{\underset{H}{\overset{|}{C^*}}}-\overset{R^8}{\underset{R^8}{\overset{|}{C}}}-OH$$

in which C* is an asymmetric carbon atom, $R^7$ and $R^8$ which may be the same or different, are alkyl, aralkyl, aryl or alkaryl or $$\underset{(CHOR^{10})_m \quad (CHOR^{14})_p}{\overset{R^{11}}{\underset{OR^9}{\bigcirc}}\overset{O}{\underset{R^{13}}{\bigcirc}}\overset{R^{12}}{\underset{R^{13}}}}$$

in which at least the ring carbon atom to which the iminyl nitrogen atom is attached is asymmetric, at least one of the carbon atoms adjacent the said carbon atom bears a hydroxyl group, $R^9$ and $R^{14}$, which may be the same or different, are hydrogen or lower alkyl, $R^{10}$ is hydrogen or lower alkyl or, where m is 1 and $R^{11}$ is $-CH_2OR^{15}$, $OR^{10}$ and $OR^{15}$ together form an acetal residue, $R^{11}$ is hydrogen or $-CH_2-OR^{15}$ in which $R^{15}$ is hydrogen, lower alkyl or where m is 1, $OR^{10}$ and $OR^{15}$ together form an acetal residue, $R^{12}$ is hydrogen or $-CH_2-OR^{15a}$ in which $R^{15a}$ is hydrogen, or a lower alkyl, $R^{13}$ is hydrogen or $OR^1$, provided that both $R^{12}$ and $R^{13}$ are not hydrogen, m is 0, 1 or 2 p is 0 or 1 provided that m plus p is 0, 1, 2 or 3; and the corresponding compounds having an oxygen atom attached to the nitrogen atom of the pyridine ring.

2. A chiral Schiff base as claimed in claim 1 wherein $R^1$, $R^2$, $R^3$ and $R^6$ are hydrogen and n is 0.

3. A chiral Schiff base as claimed in claim 1 wherein $R^7$ is a phenyl group and $R^8$ is a phenyl group having a substituent at least at the 2 position.

4. A chiral Schiff base as claimed in claim 1 wherein $R^9$ is hydrogen, $R^{10}$ is hydrogen or with $R^{15}$ forms a divalent hydrocarbon group, $R^{11}$ is $-CH_2OR^{15}$, $R^{12}$ is hydrogen, $R^{13}$ is lower alkoxy, m is 1 and p is 0.

5. A chiral Schiff base as claimed in claim 1 wherein the asymmetric carbon atom has the R or S configuration.

6. A chiral Schiff base as claimed in claim 5 wherein at least one of the groups J and K has the general structure represented by the modified Haworth projection formula:

$$\underset{OR^9}{\overset{CH_2OR^{15}}{R^{10}O \bigcirc OR^{13}}}$$

7. A chiral Schiff base as claimed in claim 5 wherein at least one of the groups J and K has the general structure represented by the formula

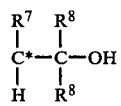

wherein the asymmetric carbon atom has the S configuration.

8. A metal complex which comprises a metal from the first or second series of the main group of transition metals in co-ordination with a chiral Schiff base as claimed in claim 1.

9. A metal complex as claimed in claim 8 in which the transition metal is selected from the group consisting of copper (II), chromium (II), manganese (II), iron (II), cobalt (II), nickel (II) and palladium (II).

10. A metal complex as claimed in claim 9 in which the transition metal is copper (II).

11. A metal complex as claimed in claim 8 which has the general structure

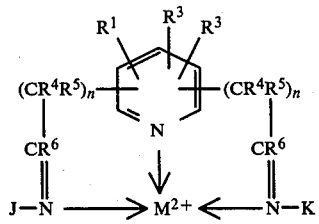

wherein $R^1$, $R^2$, $R^3$, $R^4$, $R^5$, $R^6$, J, K, and n are as defined in claim 1 and M is a metal from the first or second series of the main group of transition metals.

12. A process for preparing a Schiff base as claimed in claim 1 which process comprises reacting a compound of general formula:

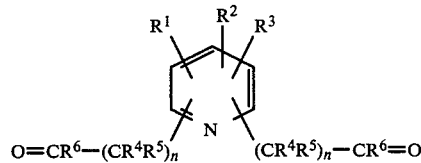

with a compound of general formula:

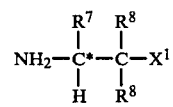

and/or with a compound of general formula:

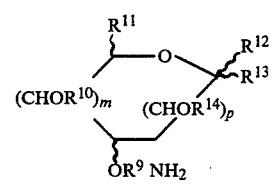

wherein C* are asymmetric carbon atoms, $X^1$ is a hydroxyl, and $R^{1-14}$, m, n, and p are as defined in claim 1.

13. A process for preparing a chiral transition metal complex as claimed in claim 8 which process comprises:
reacting a chiral Schiff base as claimed in claim 1 with a transition metal salt of an inorganic acid.

14. A process for preparing a chiral transition metal complex as claimed in claim 8 which process comprises reacting a chiral Schiff base as claimed in claim 1 with a suitable transition complex.

15. A process for preparing a chiral transition metal complex as claimed in claim 8 which process comprises reacting a chiral Schiff base as claimed in claim 1 with a suitable transition metal carboxylate.

* * * * *